(12) United States Patent
Baker et al.

(10) Patent No.: US 11,745,002 B2
(45) Date of Patent: Sep. 5, 2023

(54) MICRONEEDLE ARRAY ASSEMBLY AND FLUID DELIVERY APPARATUS HAVING SUCH AN ASSEMBLY

(71) Applicant: Sorrento Therapeutics, Inc., San Diego, CA (US)

(72) Inventors: Andrew T. Baker, Norcross, GA (US); Russell F. Ross, Jacksonville Beach, FL (US)

(73) Assignee: SORRENTO THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 17/699,708

(22) Filed: Mar. 21, 2022

(65) Prior Publication Data
US 2022/0211989 A1   Jul. 7, 2022

Related U.S. Application Data

(63) Continuation of application No. 16/095,226, filed as application No. PCT/US2017/027891 on Apr. 17, 2017, now Pat. No. 11,311,708.

(60) Provisional application No. 62/329,444, filed on Apr. 29, 2016.

(51) Int. Cl.
*A61M 37/00* (2006.01)

(52) U.S. Cl.
CPC ... *A61M 37/0015* (2013.01); *A61M 2037/003* (2013.01); *A61M 2037/0023* (2013.01); *A61M 2037/0053* (2013.01); *A61M 2037/0061* (2013.01); *A61M 2206/10* (2013.01)

(58) Field of Classification Search
CPC ...... A61M 37/0015; A61M 2037/0023; A61M 2037/003; A61M 2037/0053; A61M 2037/0061; A61K 9/0021
See application file for complete search history.

(56) References Cited

U.S. PATENT DOCUMENTS

| 6,637,463 | B1 | 10/2003 | Lei et al. |
| 10,865,334 | B2 | 12/2020 | Van Spronsen et al. |
| 2007/0043320 | A1 | 2/2007 | Kenany et al. |

(Continued)

FOREIGN PATENT DOCUMENTS

| CN | 1582174 | 2/2005 |
| CN | 102770256 A | 11/2012 |

(Continued)

OTHER PUBLICATIONS

Search Report for Chinese Patent Application No. 202111170659.8, dated Nov. 24, 2022, 3 pages.

(Continued)

*Primary Examiner* — Tasnim Mehjabin Ahmed
(74) *Attorney, Agent, or Firm* — BAKER BOTTS L.L.P.

(57) ABSTRACT

A microneedle array assembly includes a microneedle array that has a plurality of microneedles. A distribution manifold includes a fluid supply channel that is coupled in flow communication to a plurality of resistance channels. Each of the resistance channels are coupled in flow communication to a respective one of the microneedles of the microneedle array. The resistance channels have a resistance value to a fluid flow through each resistance channel that is in the range between about 5 times greater to about 100 times greater than a resistance to the fluid flow through the supply channel.

20 Claims, 12 Drawing Sheets

(56) References Cited

U.S. PATENT DOCUMENTS

| | | | |
|---|---|---|---|
| 2008/0081114 A1 | 4/2008 | Johanson et al. | |
| 2010/0190087 A1* | 7/2010 | Yoshida | H01M 8/04201 |
| | | | 429/483 |
| 2011/0306853 A1 | 12/2011 | Black et al. | |
| 2012/0220980 A1* | 8/2012 | Ross | A61M 37/0015 |
| | | | 604/173 |
| 2016/0068385 A1 | 3/2016 | Chen et al. | |
| 2017/0007812 A1* | 1/2017 | Onozuka | A61M 37/0015 |
| 2019/0143090 A1 | 5/2019 | Baker | |
| 2019/0314571 A1 | 10/2019 | Ross | |

FOREIGN PATENT DOCUMENTS

| | | |
|---|---|---|
| CN | 103384545 | 11/2013 |
| CN | 105073179 | 11/2015 |
| CN | 105209104 | 12/2015 |
| EP | 1852142 | 11/2007 |
| JP | 2007505702 A | 3/2007 |
| JP | 6239976 | 11/2017 |
| JP | 2015139547 | 8/2018 |
| WO | 3030984 | 4/2003 |
| WO | 2009038198 | 3/2009 |
| WO | 2011075099 | 6/2011 |
| WO | 2015115455 | 8/2015 |

OTHER PUBLICATIONS

EPO Search Report for related application 117790113.9 dated Nov. 25, 2019; 10 pp.
Extended European Search Report for Patent Application EP 20210798.3 dated May 12, 2021; 8 pp.
Search Report for CN Patent Application 201780026217.1 dated Mar. 15, 2021; 2 pp.
AU Examination Report for Application AU 2017258750 dated Apr. 30, 2021; 4 pp.
Translation of Notice of Grounds for Rejection for Patent Application JP 2018-556458 dated Feb. 24, 2021; 5 pp.
CN First Office Action for China Patent Application 201780026217.1 dated Sep. 2, 2020; 13 pp.
International Search Report and Written Opinion of International Application No. PCT/US2017/027891, dated Oct. 30, 2017, 13 pages.
Notice of Preliminary Rejection for Patent Application KR 10-2018-7034189 dated Sep. 7, 2021; 8 pp.
Second Office Action for JP Pat. Appl. No. 2018-556458 dated Oct. 5, 2021 (translation only), 2 pages.
Japanese Office Action for Japanese Application No. 2022-37240; English Translation, 7 pages.

* cited by examiner

MICRONEEDLE ARRAY ASSEMBLY AND FLUID DELIVERY APPARATUS HAVING SUCH AN ASSEMBLY

CROSS-REFERENCE TO RELATED APPLICATIONS

This application is a continuation of U.S. patent application Ser. No. 16/095,226, filed Oct. 19, 2018, which is a 35 U.S.C. § 371 national phase application of PCT Application PCT/US2017/027891, filed Apr. 17, 2017, which claims the benefit of U.S. Provisional Ser. No. 62/329,444, filed Apr. 29, 2016, the entire contents of each of which are incorporated herein by reference.

FIELD OF THE DISCLOSURE

The present disclosure relates generally to a fluid delivery apparatus, and more particularly to a microfluidic distribution manifold for use with a microneedle assembly of the fluid delivery apparatus.

BACKGROUND OF THE DISCLOSURE

Numerous apparatus have been developed for transdermal delivery of medicines using microneedle assemblies. Microneedle assemblies facilitate reducing an amount of pain felt by a patient as compared to larger conventional needles. Conventional subcutaneous (and often intra-muscular) delivery of medicines using a needle operates to deliver a large quantity of the medicine at one time, thereby creating a spike in the bioavailability of the medicine. While this is not a significant problem for some medicines, many medicines benefit from having a steady state concentration in the patient's blood stream. Transdermal delivery apparatus are capable of slowly administering drugs at a substantially constant rate over an extended period of time. However, the quantity of the medicine delivered through each microneedle of the microneedle assembly may not be equal. Alternatively, transdermal drug delivery apparatus may administer drugs at variable rates. Thus, transdermal drug delivery apparatus offer several advantages relative to conventional subcutaneous drug delivery methods.

BRIEF DESCRIPTION

In one aspect, a microneedle array assembly is provided. The microneedle array assembly includes a microneedle array including a plurality of microneedles, and a distribution manifold including a supply channel. The supply channel is coupled in flow communication to a plurality of resistance channels. Each resistance channel is coupled in flow communication to a respective one of the plurality of microneedles. A resistance value to a fluid flow through each resistance channel of the plurality of resistance channels is in the range between about 5 times greater to about 100 times greater than a resistance to the fluid flow through the supply channel.

In another aspect, a fluid delivery apparatus is provided. The fluid delivery apparatus includes a reservoir containing a fluid, and a microneedle array assembly. The microneedle array assembly includes a microneedle array having a plurality of fluid channels formed in an upstream side, and a plurality of a plurality of microneedles extending from a downstream side. Each microneedle is coupled in flow communication to a respective one of the plurality of fluid channels. The microneedle array also includes a distribution manifold having a supply channel coupled in flow communication to the plurality of fluid channels. A resistance value to a fluid flow through each fluid channel of the plurality of fluid channels is in the range between about 5 times greater to about 100 times greater than a resistance to the fluid flow through the supply channel.

In yet another aspect, a microneedle array assembly is provided. The microneedle array assembly includes a microneedle array having a plurality of microneedles. Each microneedle of the plurality of microneedles includes an aperture. The microneedle array also includes a distribution manifold having an inlet channel, a plurality of supply channels formed in a downstream surface of the distribution manifold, and a plurality of outlet channels. Each of the supply channels is coupled in flow communication to the inlet channel and a respective one of the plurality of outlet channels. A pressure drop between the inlet channel and each outlet channel of the plurality of outlet channels is substantially the same.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

Unless otherwise indicated, the drawings provided herein are meant to illustrate features of embodiments of the disclosure. These features are believed to be applicable in a wide variety of systems comprising one or more embodiments of the disclosure. As such, the drawings are not meant to include all conventional features known by those of ordinary skill in the art to be required for the practice of the embodiments disclosed herein.

DETAILED DESCRIPTION

In the following specification and the claims, reference will be made to a number of terms, which shall be defined to have the following meanings. The singular forms "a," "an," and "the" include plural references unless the context clearly dictates otherwise. The terms "comprising," "including," and "having" are intended to be inclusive and mean that there may be additional elements other than the listed elements. "Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value, Here and throughout the specification and claims, range limitations may be combined and/or interchanged; such ranges are identified and include all the sub-ranges contained therein unless context or language indicates otherwise.

As used herein, positional terms such as upward, downward, upper, lower, top, bottom, and the like are used only for convenience to indicate relative positional relationships.

Figure 1:
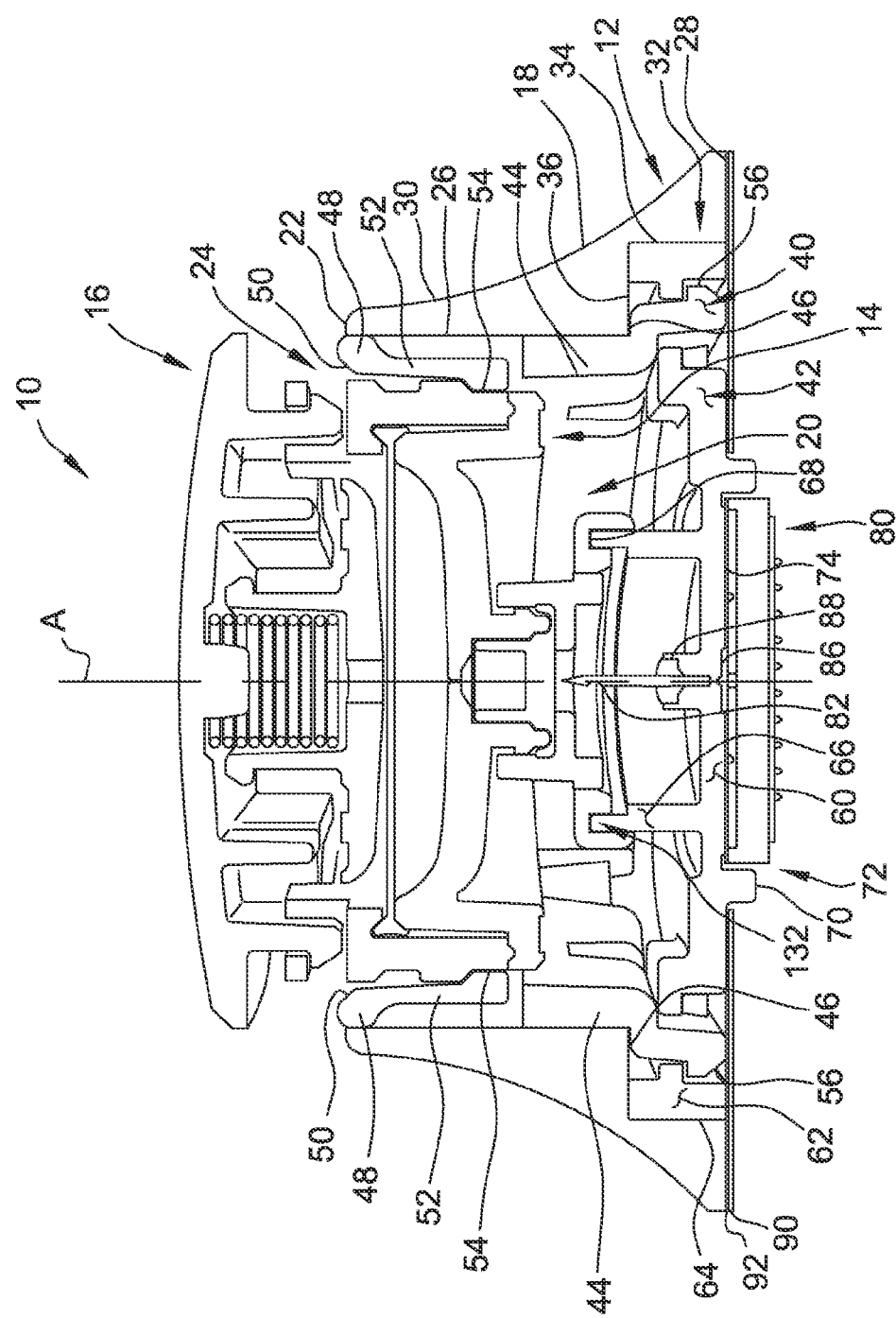
FIG. 1 is a sectional view of an exemplary fluid delivery apparatus.

Referring now to the drawings, FIG. 1 is a sectional view of an exemplary fluid delivery apparatus 10 (e.g., a drug delivery apparatus). In the exemplary embodiment, the fluid delivery apparatus 10 includes a plurality of subassembly components coupled together to form the fluid delivery apparatus 10, including a receptacle 12, a cartridge 14, and a mechanical controller 16. Each of the receptacle 12, the cartridge 14, and the mechanical controller 16 is indicated generally in the accompanying drawings. The receptacle 12, as seen in FIG. 1, forms the body of the fluid delivery apparatus 10 and is slidably coupled to the cartridge 14. In addition, the mechanical controller 16, as explained in more detail below, is coupled to the cartridge 14.

In the exemplary embodiment, the receptacle 12 includes an outer body 18 formed in a generally frustoconical shape and having an interior space 20 defined therein. The outer body is formed substantially symmetrically about a central axis "A." An upper rim 22 of the body 18 defines an opening 24 to the interior space 20. An inner surface 26 extends generally vertically downward from the rim 22 towards a base wall 28 of the body 18 and extends around the interior space 20. As illustrated in FIG. 1, the outer body 18 includes a curved outer surface 30 that is generally inclined inward as it extends upward from the base wall 28 to the rim 22. A notch 32 extends around the interior space 20 and is formed at an intersection of the inner surface 26 and the base wall 28. The notch includes and generally vertical outer wall 34 and a generally horizontal upper wall 36.

In the exemplary embodiment, the receptacle 12 further includes a controller support structure 40 coupled to the body 18 within the interior space 20, and a microneedle array support structure 42 coupled to the notch 32 of the body 18. In addition, the controller support structure 40 is coupled to the microneedle array support structure 42.

The controller support structure 40 includes a lower annular wall portion 44 that extends vertically downward beyond the horizontal upper wall 36 of the notch 32. The lower wall portion 44 includes a flange portion 46 that extends radially outward from the lower wall portion 44 and is configured to engage the horizontal upper wall 36 of the notch 32. The flange portion 46 includes a plurality of latch members 56 configured to engage and couple to at least a portion of microneedle array support structure 42. At an upper wall portion 48, the controller support structure 40 includes an inner beveled surface 50 and a plurality of spaced flexible tabs 52 that extend radially inward from the inner surface 26 of the body 18. Each of the flexible tabs 52 includes an inward extending protrusion 54 at the free end of the flexible tab. The inward extending protrusions 54 are configured to engage the cartridge 14.

In the exemplary embodiment, the microneedle array support structure 42 includes a generally planar body portion 60 that extends horizontally across the interior space 20 of the body 18. A peripheral wall 62 extends vertically upward about a periphery of the body portion 60 and includes and outer surface 64 configured to engage the vertical outer wall 34 of the notch 32. In particular, the peripheral wall 62 is formed substantially parallel to the vertical outer wall 34 and is sized to couple to the vertical outer wall 34 via an interference fit. As used herein, the phrase "interference fit" means a value of tightness between the vertical outer wall 34 and the peripheral surface 60, i.e., an amount of radial clearance between the components. A negative amount of clearance is commonly referred to as a press fit, where the magnitude of interference determines whether the fit is a light interference fit or an interference fit. A small amount of positive clearance is referred to as a loose or sliding fit.

The microneedle array support structure 42 also includes a vertically upward extending central wall 66 located proximate a central portion of the body portion 60. As illustrated in FIG. 1, the central wall 66 includes an upper rim 68 configured to couple to the cartridge 14. The microneedle array support structure 42 also includes a frame portion 70 that extends vertically downward from the body portion 60. The frame portion 70 defines a mounting space 72 for coupling a microneedle array assembly 80 to a mounting surface 74 located within the mounting space 72.

In addition, with continued reference to FIG. 1, the microneedle array support structure 42 includes at least one cannula 82 coupled to a mount 84 extending upward from the microneedle array support structure 42. In particular, a lower portion of the cannula 82 is coupled in fluid communication with a fluid passage 86 extending through the microneedle array support structure 42 via an interference fit with the mount 84. Alternatively, the cannula 82 may be coupled to the mount 84 using any suitable fastening technique, for example, adhesive bonding, that enables the microneedle array support structure 42 to function as described herein. In the exemplary embodiment, an upper portion the cannula 82 is sharply pointed and extends upward away from the microneedle array support structure 42, such that the cannula 84 can pierce a portion of the cartridge 14. As illustrated, the cannula 82 extends upward through a sealing gasket 88 coupled to the mount 84 and configured to seal the fluid passage 86.

In the exemplary embodiment, the microneedle array support structure 42 includes a protective release paper backing 90 extending substantially entirely over an adhesive layer 92 that is coupled to the base wall 28 of the body 18 and at least a portion of the lower surface of the microneedle array support structure 42. The adhesive layer 92 is configured to couple the fluid delivery apparatus 10 to a user's skin surface. The release paper backing 90 is configured to prevent the adhesive layer 92 from coupling to the user, or any other object, before use of the fluid delivery apparatus 10.

Figure 2:
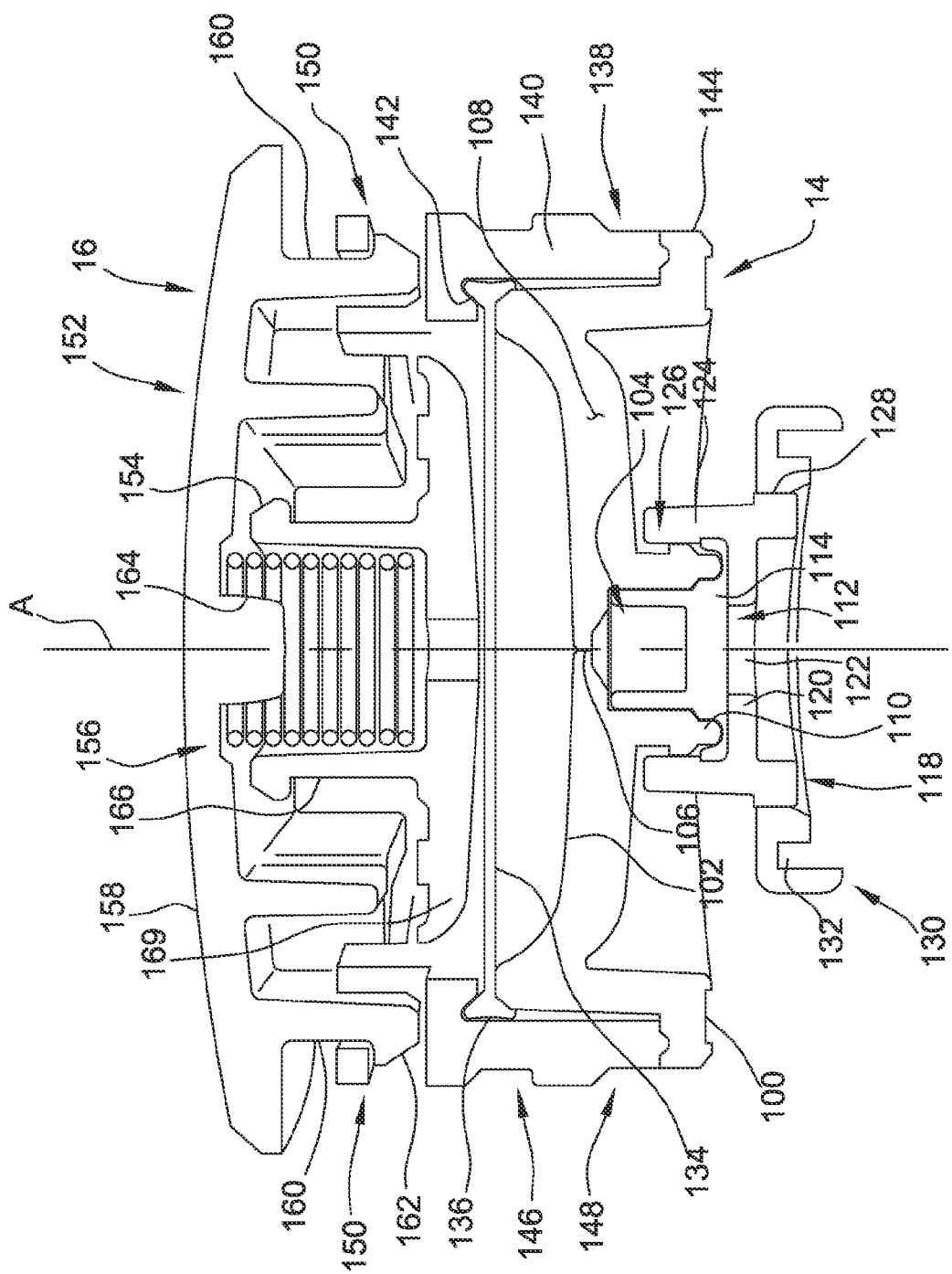
FIG. 2 is a sectional view of a cartridge and a mechanical controller of the fluid delivery apparatus shown in FIG. 1.

FIG. 2 is a sectional view of the cartridge 14 and the mechanical controller 16 of the fluid delivery apparatus 10 shown in FIG. 1. In the exemplary embodiment, the cartridge 14 includes a central body 100 having central axis "A." The central body 100 includes an upper cavity 102 and an opposing lower cavity 104 coupled together in flow communication via a fluid passage 106. In the exemplary embodiment, the upper cavity 102 has a generally concave cross-sectional shape, defined by a generally concave body portion 108 of the central body 100. The lower cavity 104 has a generally rectangular cross-sectional shape, defined by a lower wall 110 that extends generally vertically downward from a central portion of the concave body portion 108. An upper portion of the end of the fluid passage 106 is open at the lowest point of the upper cavity 102, and an opposite lower portion of the fluid passage 106 is open at a central portion of the lower cavity 104. The lower portion of the fluid passage 106 expands outward at the lower cavity 104, forming a generally inverse funnel cross-sectional shape. In other embodiments, the cross-sectional shapes of the upper cavity 102, the lower cavity 104, and the fluid passage 106 may be formed in any configuration that enables the central body 100 to function as describe herein.

In the exemplary embodiment, the cartridge 14 includes a lower sealing member 112 configured to couple to the central body 100 and close the lower cavity 104. The lower sealing member is formed by a lower wall 114 that includes a peripheral channel configured to sealingly engage a rim of the lower wall 100 of the central body 100. Extending axially, into the lower cavity 104, is an upper seal wall 116. A lower cap 118 extends over the lower sealing member 112 and is configured to fixedly engage the lower wall 110 of the central body 100. This facilitates securing the lower sealing member 112 in sealing contact with the central body 100, thereby closing the lower cavity 104.

The lower cap 118 includes a lower wall 120 having a centrally located opening 122 that enables access to the lower wall 114 of the sealing member 112. The lower cap 118 includes a vertically-extending wall 124 that extends upward and downward from a peripheral edge of the lower wall 120. In the exemplary embodiment, an upper portion of the vertically-extending wall 124 engages the lower wall 110 of the central body 100 via a mechanical latching connection, as indicated at 126. In other embodiments, the vertically-extending wall 124 may engage the lower wall 110 of the central body 100 using any connection technique that enables the lower cap 118 to fixedly engage the lower wall 110, for example, via an interference fit, an adhesive bond, a weld joint (e.g., spin welding, ultrasonic welding, laser welding, or heat staking), and the like. In the exemplary embodiment, a lower portion of the vertically-extending wall 124 forms a peripheral sealing surface 128 configured to engage a seal member 130. As illustrated, the seal member 130 includes a channel 132 configured to frictionally engage the upper rim 68 of the central wall 66, as described herein.

In the exemplary embodiment, the cartridge 14 also includes an upper sealing member 134 or membrane configured to couple to the central body 100 and close the upper cavity 102. The upper sealing member 134 is formed as a generally flat sealing membrane and includes a peripheral ridge member 136 to facilitate sealingly securing the upper sealing member 134 to the central body 100. An upper cap 138 extends over the upper sealing member 134 and is configured to fixedly engage the central body 100. This facilitates securing the upper sealing member 134 in sealing contact with the central body 100, thereby closing the upper cavity 102.

As illustrated in FIG. 2, the upper cap 138 includes a vertically-extending wall 140 that has an inward extending flange member 142 configured to couple to the peripheral ridge member 136 of the upper sealing member 134. In particular, the flange member 142 cooperates with the wall concave body portion 108 of the central body 100 to compress and sealingly secure the upper sealing member 134 therebetween. In the exemplary embodiment, a lower end of the vertically-extending wall 140 is coupled to a coupling flange 144 of the central body 100 via a weld joint, for example, spin welding, ultrasonic welding, laser welding, or heat staking. In other embodiments, the vertically-extending wall 140 may be coupled to a coupling flange 144 using any connection technique that enables the upper cap 138 to fixedly engage the central body 100, for example, via an adhesive bond and the like.

In the exemplary embodiment, the upper cap 138 also includes upper and lower grooves 146 and 148, respectively, formed in an outer surface of the vertically-extending wall 140. The upper and lower grooves 146 and 148 are configured to engage the plurality of spaced flexible tabs 52 of the body 18, and, in particular, the inward extending protrusions 54 at the free end of the flexible tabs 52, as is described herein. In addition, the upper cap 138 also includes a plurality of latch receiving openings 150 at an upper portion of the vertically-extending wall 140. The latch receiving openings 150 are configured to couple to the mechanical controller 16 to secure it to the cartridge 14.

With continued reference to FIG. 2, in the exemplary embodiment, the mechanical controller 16 includes at least a controller housing 152, a plunger member 154, and a bias member 156 located between the controller housing 152 and the plunger member 154 for biasing the plunger member 154 in an axial direction away from the controller housing 152. In the exemplary embodiment, the bias member 156 is a compression spring. Alternatively, the bias member 156 may be any type of bias or force provider that enables the mechanical controller 16 to function as describe herein.

In the exemplary embodiment, the controller housing 152 includes an upper wall 158 having a curved or dome-shaped cross-sectional profile. Extending generally vertically-downward from the upper wall 158 are a plurality of flexible tabs 160 configured for latching engagement with the latch receiving openings 150 of the upper cap 138. Each flexible tab 160 includes an inward extending protrusion 162 at the free end of the flexible tab 160 to provide a latching connection with a respective receiving opening 150, as illustrated in FIG. 2. In addition, the controller housing 152 includes a bias member guide 164 extending downward coaxially from the upper wall 158 for extending into, and facilitating locating, the bias member 156.

The plunger member 154 includes a guide wall 166 coaxially extending vertically-upward from a domed head 168. As illustrated, the guide wall is configured to receive the bias member 156 therein, and extend around the bias member guide 164. The domed head 168 is configured to engage the upper sealing member 134 of the cartridge 14 via force applied by the bias member 156 during use of the fluid delivery apparatus 10.

As described herein with respect to FIG. 1, the fluid delivery apparatus 10 includes a microneedle array assembly 80 coupled to the mounting surface 74 located within the mounting space 72 of the microneedle array support structure 42. While the microneedle array assembly 80 is described herein as being used with the exemplary fluid delivery apparatus 10, it is contemplated that the microneedle array assembly 80 may be used, or otherwise incorporated into other suitable fluid delivery device. For example, the fluid delivery apparatus 10 may be replaced with other suitable devices for delivering a fluid to an inlet or inlet channel of the microneedle array 80.

Figure 3:
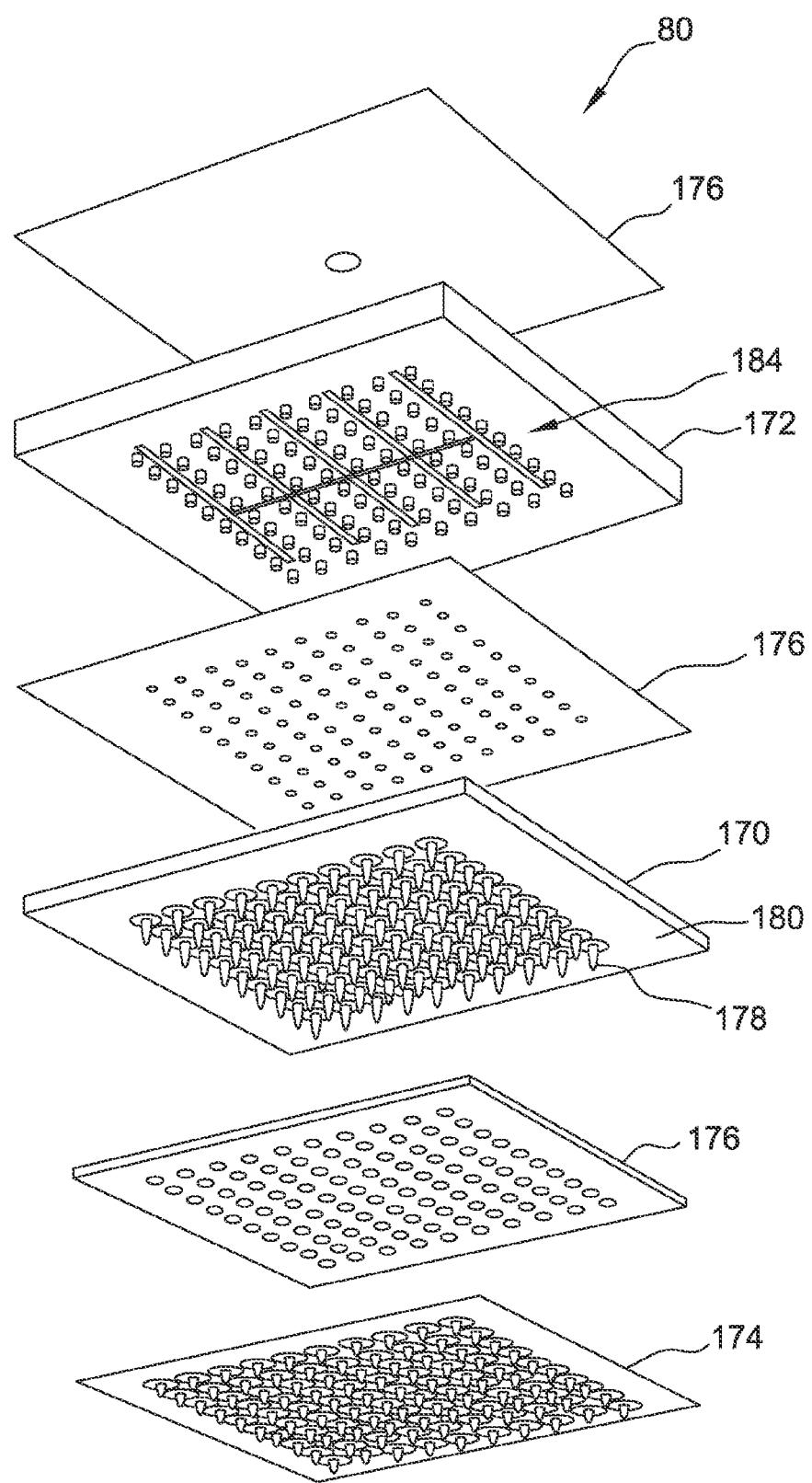
FIG. 3 is an exploded schematic of an exemplary microneedle array assembly for use with the fluid delivery apparatus shown in FIG. 1.
Figure 4:
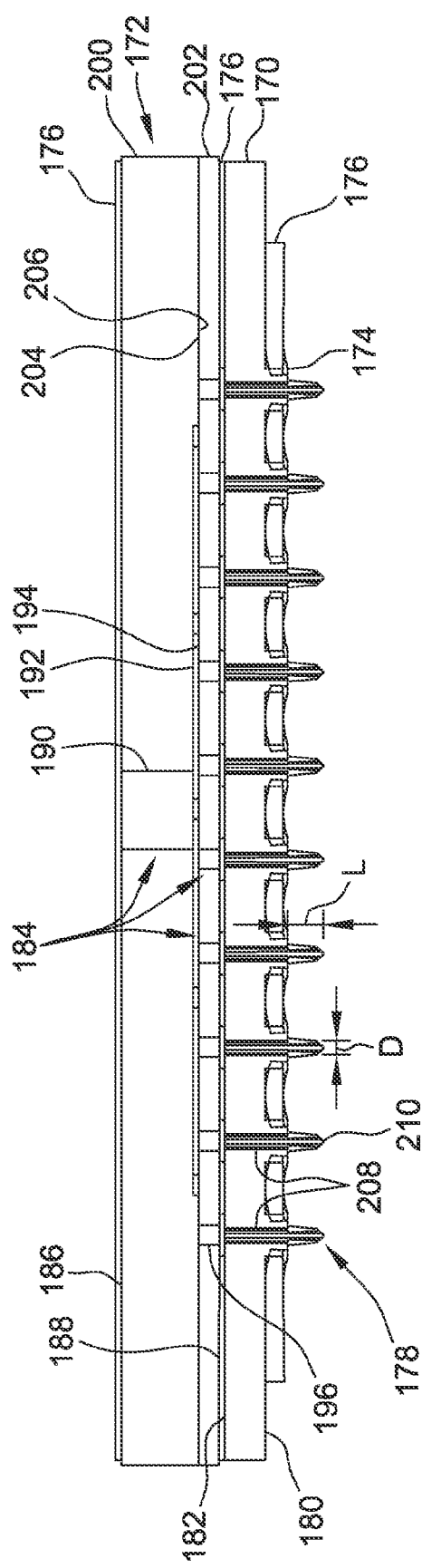
FIG. 4 is a schematic cross-sectional view of the microneedle array assembly of FIG. 3.

FIG. 3 is an exploded schematic of an exemplary microneedle array assembly 80 for use with the fluid delivery apparatus 10 shown in FIG. 1. FIG. 4 is a schematic cross-sectional view of the microneedle array assembly 80 of FIG. 3. In the exemplary embodiment, the microneedle array assembly 80 is bonded to the mounting surface 74 via an adhesive layer 176. The microneedle array assembly 80 includes a microneedle array 170 and a membrane 174 draped at least partially across a plurality of microneedles 178 and a base surface 180 of the microneedle array 170. The microneedle array assembly 80 also includes a distribution manifold 172 that extends across a back surface 182 of the microneedle array 170 and is bonded thereto by an additional adhesive layer 176. The distribution manifold 172 includes a fluid distribution network 184 for providing a fluid to the microneedle array 170. The fluid supplied from the distribution manifold 172 may be in the form of a liquid drug formulation. The membrane-draped microneedles 178 are configured to penetrate a user's skin, such as for providing the liquid drug formulation into the users skin by way of one or more apertures formed in each microneedle 178.

In the exemplary embodiment, the draped membrane 174 may be fabricated from a polymeric (e.g., plastic) film, or the like, and coupled to the microneedle array 170 using adhesive 176. In other embodiments, the draped membrane 174 may include an embossed or nano-imprinted, polymeric (e.g., plastic) film, or be fabricated from a polyether ether ketone (PEEK) film that is about five microns thick, or the draped membrane may be any other suitable material, such as a polypropylene film. It is contemplated that the microneedle array assembly 80 may not include the draped membrane 174 in some embodiments.

In the exemplary embodiment, the microneedle array 170 may be fabricated from a rigid, semi-rigid, or flexible sheet of material, for example, without limitation, a metal material, a ceramic material, a polymer (e.g., plastic) material, or any other suitable material that enables the microneedle array 170 to function as described herein. For example, in one suitable embodiment, the microneedle array 170 may be formed from silicon by way of reactive-ion etching, or in any other suitable fabrication technique.

As shown in FIG. 4, the microneedle array 170 includes a plurality of microneedles 178 that extend outwardly from the back surface 182 of the microneedle array 170. The microneedle array 170 includes a plurality of passageways 208 extending between the back surface 182 for permitting the fluid to flow therethrough. For example, in the exemplary embodiment, each passageway 208 extends through the microneedle array 170 as well as through the microneedle 178.

Each microneedle 178 includes a base that extends downwardly from the back surface 182 and transitions to a piercing or needle-like shape (e.g., a conical or pyramidal shape or a cylindrical shape transitioning to a conical or pyramidal shape) having a tip 210 that is distant from the back surface 182. The tip 210 of each microneedle 178 is disposed furthest away from the microneedle array 170 and defines the smallest dimension (e.g., diameter or cross-sectional width) of each microneedle 178. Additionally, each microneedle 178 may generally define any suitable length "L" between the base surface 180 of the microneedle array 170 its tip 210 that is sufficient to allow the microneedles 178 to penetrate the user's skin. In the exemplary embodiment, each microneedle 178 has a length L of less than about 1000 micrometers (um). Each microneedle 178 may generally have any suitable aspect ratio (i.e., the length L over a cross-sectional width dimension D of each microneedle 178). The aspect ratio may be greater than 2, such as greater than 3 or greater than 4. In instances in which the cross-sectional width dimension (e.g., diameter) varies over the length of each microneedle 31, the aspect ratio may be determined based on the average cross-sectional width dimension.

The channels or passageways 208 of each microneedle 178 may be defined through the interior of the microneedles 178 such that each microneedle forms a hollow shaft, or may extend along an outer surface of the microneedles to form a downstream pathway that enables the fluid to flow from the back surface 182 of the microneedle array 170 and through the passageways 208, at which point the fluid may be delivered onto, into, and/or through the user's skin. The passageways 208 may be configured to define any suitable cross-sectional shape, for example, without limitation, a semi-circular or circular shape. Alternatively, each passageway 208 may define a non-circular shape, such as a "v" shape or any other suitable cross-sectional shape that enables the microneedles 178 to function as described herein.

The microneedle array 170 may generally include any suitable number of microneedles 178 extending from back surface 182. For example, in some suitable embodiments, the quantity of microneedles 178 included within the microneedle array 170 is in the range between about 10 microneedles per square centimeter ($cm^2$) to about 1,500 microneedles per $cm^2$. The microneedles 178 may generally be arranged in a variety of different patterns. For example, in some suitable embodiments, the microneedles 178 are spaced apart in a uniform manner, such as in a rectangular or square grid or in concentric circles. In such embodiments, the spacing of the microneedles 178 may generally depend on numerous factors, including, but not limited to, the length and width of the microneedles 31, as well as the amount and type of liquid formulation that is intended to be delivered through or along the microneedles 31.

Figure 5:
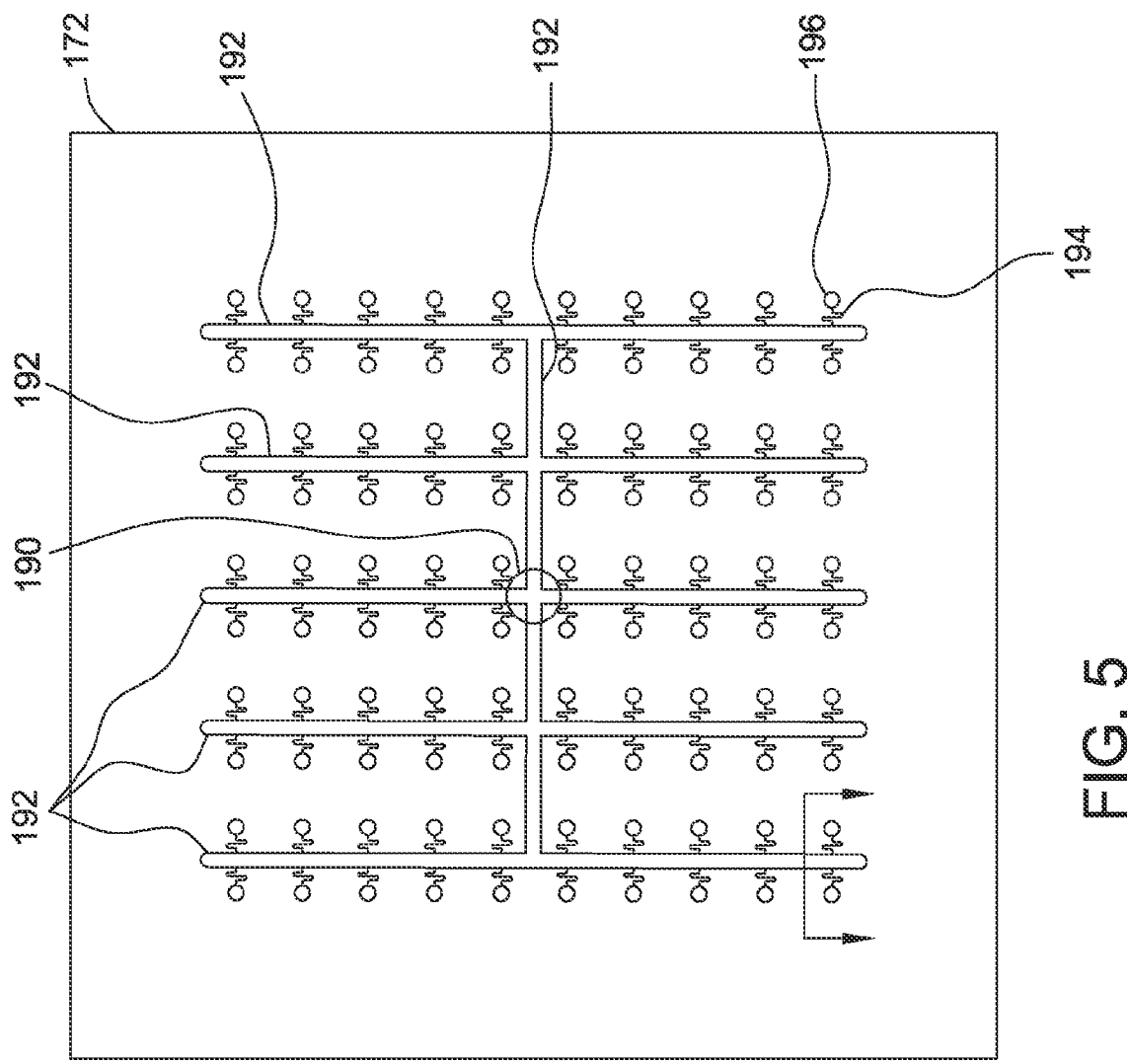
FIG. 5 is a schematic plan view of a distribution manifold for use with the microneedle array of FIG. 3.
Figure 6:
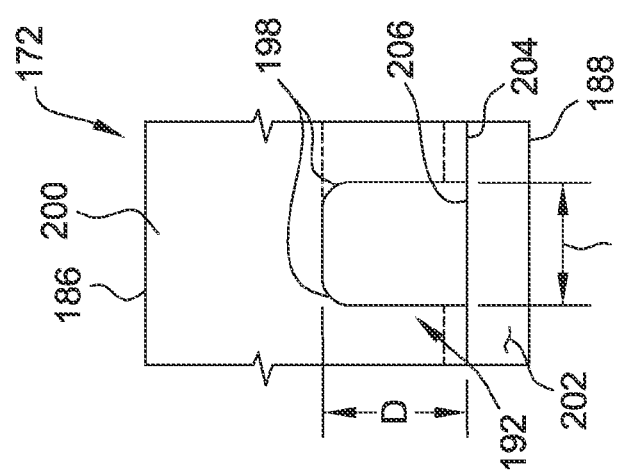
FIG. 6 is a sectional view of the distribution manifold taken about line A-A, illustrating an exemplary profile of a supply channel.

FIG. 5 is a schematic plan view of the distribution manifold 172 for use with the microneedle array 170 of FIG. 3. FIG. 6 is a sectional view of the distribution manifold 172 taken about line A-A, illustrating an exemplary profile of a supply channel 192. In the exemplary embodiment, the distribution manifold 172 includes the fluid distribution network 184 formed therein. The fluid distribution network includes, for example, a plurality of channels and/or apertures extending between a top surface 186 and a bottom surface 188 of the distribution manifold 172. The channels and/or apertures include a centrally-located inlet channel 190 coupled in flow communication with a plurality of supply channels 192, and the fluid passage 86 (shown in FIG. 1) of the microneedle array support structure 42 (shown in FIG. 1). In the exemplary embodiment, the plurality of supply channels 192 include 5 substantially parallel, equispaced channels 192 extending longitudinally along the distribution manifold 172. In addition, a single supply channel 192 extends transversely across the 5 substantially parallel, equispaced channels 192 at about a midpoint of the channels. The supply channels 192 facilitate distributing a fluid supplied by the inlet channel 190 across an area of the distribution manifold 172.

Each of the 5 substantially parallel, equispaced supply channels 192 are coupled in flow communication to a plurality of resistance channels 194. The resistance channels 194 extend away from the supply channels 192 and are equispaced along the longitudinal length of the channels. In addition, the resistance channels 194 are formed symmetrically with each other along an axis of the respective supply channel 192. The resistance channels 194 have a size that is smaller than a size of the supply channels 192. Moreover, the resistance channels 194 are formed to create a tortuous flow path for the fluid, thereby facilitating an increase of the resistance of the fluid distribution network 184 to the flow of the fluid. Each one of the resistance channels 194 are coupled in flow communication to an outlet channel 196. As illustrated in FIG. 4, each outlet channel 196 is aligned with a respective microneedle 178 for distributing the fluid through the microneedles passageway 208. In other embodiments, the channels 190, 192, 194, and 196 may be formed in any configuration that enables the distribution manifold 172 to function as described herein.

In the exemplary embodiment, the supply channel 192 has a generally U-shape having a width "W" and a depth "D." A D/W ratio of the channel is configured to be in the range of about 0.2 to about 2.2. In some embodiments, corners 198 formed at the bottom of the channels, for example, the supply channel 192, are rounded to facilitate reducing the formation of bubbles in the fluid as it flows through the channels (FIG. 6). The size and shape of the channels 190, 192, 194, and 196, including the respective corners 198, is predetermined based on a desired flow rate, pressure drop, and/or fabrication limitations.

In the exemplary embodiment, the distribution manifold 172 is formed by bonding a base substrate 200 including the inlet channel 190 formed through the substrate, and the supply channels 192 and the resistance channels 194 formed in a bottom surface 204, to a cover substrate 202 including the outlet channels 196 formed therethrough. The inlet channel 190 may be formed in the substrate 200 by drilling, cutting, etching, and or any other manufacturing technique for forming a channel or aperture through substrate 200. In the exemplary embodiment, the supply channels 192 and the resistance channels 194 are formed in the bottom surface 204 of the substrate 200 using an etching technique. For example, in one suitable embodiment, wet etching, or hydrofluoric acid etching, is used to form the supply channels 192 and the resistance channels 194. A mask is applied to the bottom surface 204 of the substrate 200 to form the location of the channels to an accuracy of less than 2 micrometers, for example. The etching material (e.g., hydrofluoric acid) is applied to the bottom surface 204 to remove material from the bottom surface, thereby forming the supply channels 192 and the resistance channels 194. In general, wet etching results in a channel that has a D/W ratio of about 0.5 and rounded corners. In another suitable embodiment, Deep Reactive Ion Etching (DRIE or plasma etching) may be used to create deep, high density, and high aspect ratio structures in substrate 200. DRIE etching enables channels to be created that include steep sidewalls with variable inclination as well as sidewalls with rounded corners. Alternatively, the supply channels 192 and resistance channels 194 can be formed in bottom surface 204 using any fabrication process that enables the distribution manifold 172 to function as described herein. In the exemplary embodiment, the outlet channels 196 are formed through the cover substrate 202 by drilling, cutting, etching, and or any other manufacturing technique for forming a channel or aperture through substrate 202.

In the exemplary embodiment, the base substrate 200 and the cover substrate 202 are bonded together in face-to-face contact to seal the edges of the supply channels 192 and the resistance channels 194 of the distribution manifold 172. In one suitable embodiment, direct bonding, or direct aligned bonding, is used by creating a prebond between the two substrates 200 and 202. The prebond can include applying a bonding agent to the bottom surface 204 of the substrate 200 and the top surface 206 of the cover substrate 202 before bringing the two substrates into direct contact. The two substrates 200 and 202 are aligned and brought into face-to-face contact and annealed at an elevated temperature. In another suitable embodiment, anodic bonding is used to form the distribution manifold 172. For example, an electrical field is applied across the bond interface at surfaces 204 and 206, while the substrates 200 and 202 are heated. In an alternative embodiment, the two substrates 200 and 202 may be bonded together by using a laser-assisted bonding process, including applying localized heating to the substrates 200 and 202 to bond them together.

In the exemplary embodiment, the base substrate 200 and the cover substrate 202 are fabricated from a glass material. Alternatively, the base substrate 200 and the cover substrate 202 may be fabricated from silicon. It is contemplated that the base substrate 200 and the cover substrate 202 may be fabricated from different materials, for example, substrate 200 may be fabricated from a glass and the substrate 202 may fabricated from a silicon. In other embodiment, the base substrate 200 and the cover substrate 202 may be fabricated from any material and material combination that enables the distribution manifold 172 to function as described herein.

With reference to FIGS. 1 and 2, during operation of the fluid delivery apparatus 10, the plunger member 154 applies a pressure to the cartridge 14 via the bias member 156 and a fluid contained in the upper cavity 102 flows through the cannula 82 into the fluid passage 86. The fluid exits the fluid passage 86 by flowing through the inlet channel 190 of the distribution manifold 172, and then the fluid flows through the supply channels 192, the resistance channels 194, and the outlet channel 196 to the passageways 208 of the microneedles 178 and into the user's skin.

In the exemplary embodiment, the bias member 156 functions in connection with the plunger member 154 to provide substantially complete emptying of the fluid from the cartridge 14 through the cannula 82 and into the fluid passage 86. The plunger member 154 and bias member 156 may provide an initial force in a range of about 32 kilopascals (kPa) (4.6 pounds per square inch (psi)) to about 120 kPa (17.4 psi). The fluid delivery apparatus 10 shown in FIG. 1 is provided as an example only. That is, the microneedle array assembly 80 may be used with or otherwise incorporated into any other suitable devices. For example, the plunger member 154, bias member 156, and/or mechanical controller 16 may be replaced with other suitable features for forcing the fluid into the fluid passage 86, or the like.

Figure 7:
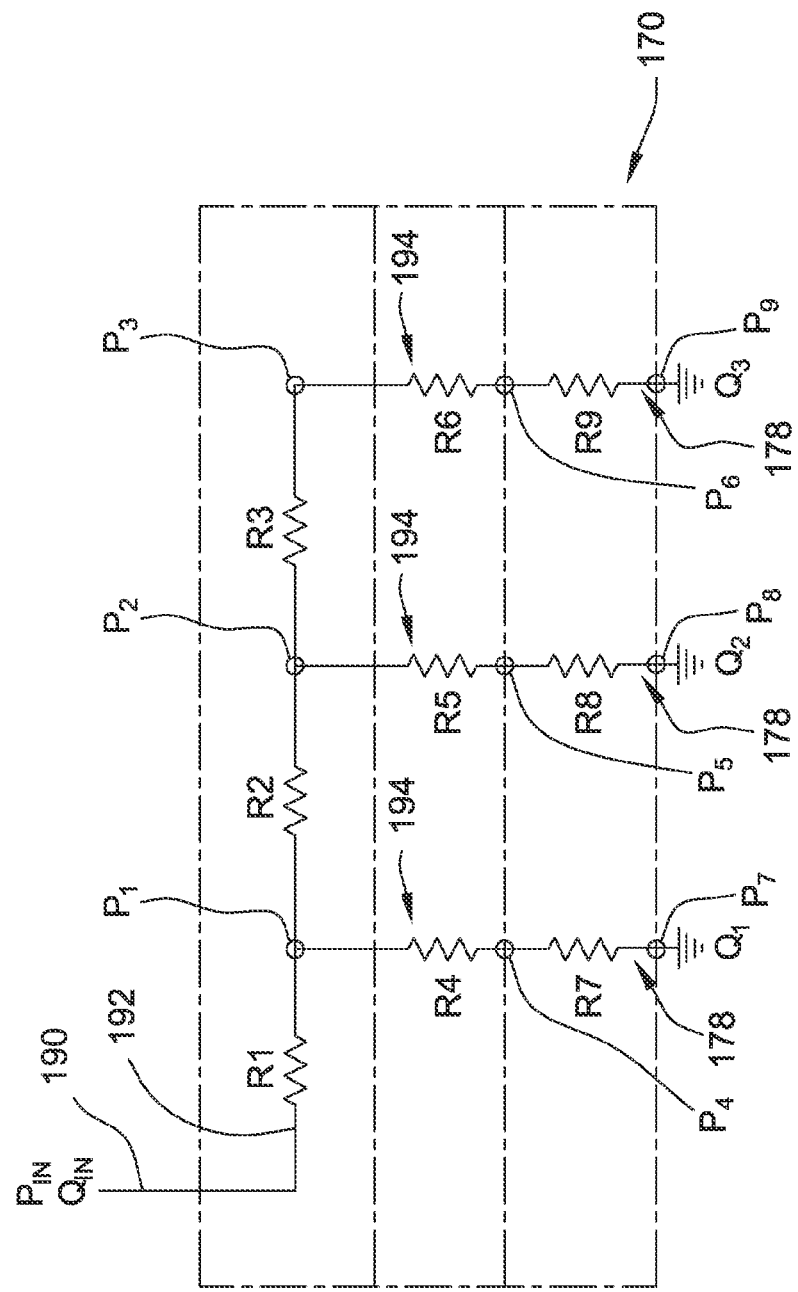
FIG. 7 is a representation of a portion of the microneedle array assembly and the resistance to a fluid flow therein.

FIG. 7 is a representation of a portion of the microneedle array assembly 80 and the resistance to a fluid flow therein. It is assumed that the fluid distribution network 184 of the microneedle array 170 is full of the fluid. The fluid flowing through the distribution manifold 172 enters the inlet channel 190 at a pressure $P_{in}$ and a flow rate $Q_{in}$, and is channeled to the supply channel 192. The flow resistance to the fluid flowing through the supply channel 192 is relatively small and is represented by R1, R2, and R3 as the fluid flows along the supply channel 192. However, as the fluid enters the resistance channels 194, the resistance to flow is substantially increased, which is represented by R4, R5, and R6, respectively. For example in one suitable embodiment, the resistance to flow through the resistance channels 194 (represented by resistance values R4, R5, and R6) is at least about 5 times greater than the resistance to flow through the supply channels 192. In some embodiments, the resistance to flow through the resistance channels 194 at least about 30 times greater than, at least about 50 times greater than, between about 5 and about 100 times greater than, between about 40 and about 100 times greater than, or between about 50 and about 100 times greater than the resistance to flow through the supply channels 192. The resistance values R4, R5, and R6 of the resistance channels 194 are significantly higher than the respective resistance values R1, R2, and R3 due, in part, by the resistance channels 194 being fabricated with a much smaller cross-sectional area than the cross-sectional area of the supply channels 192. The increased resistance values R4, R5, and R6 result in a pressure drop across the resistance channels 194 (for example, $P_4$-$P_1$, $P_5$-$P_2$, and $P_6$-$P_3$) such that fluid pressures $P_1$, $P_2$, and $P_3$ along the supply channel 192 are substantially equal. Thus, because $P_1$, $P_2$, and $P_3$ are substantially equal, the resistance channels 194 can be fabricated essentially the same size to provide substantially the same resistance values R4, R5, and R6. Flow resistance through each of the microneedles 178 of the microneedle array 170 is substantially the same and is represented by R7, R8, and R9, respectively. Thus, substantially equal pressure drops across the microneedles 178 (for example, $P_7$-$P_4$, $P_8$-$P_5$, and $P_9$-$P_6$) result in flow rates $Q_1$, $Q_2$, and $Q_3$ at respective microneedles 178 being substantially the same. In the exemplary embodiment, the flow rate through each microneedle 178 is in the range between about 0.1 microliter per hour (uL/hr) to about 20.0 uL/hr. In some suitable embodiments, the flow rate through each microneedle 178 is in the range between about 0.25 uL/hr to about 5.0 uL/hr, and preferably, about 1 uL/hr.

Thus, in the exemplary embodiment, by substantially increasing the resistance value across the resistance channels 194, the theoretical difference in pressures, e.g., $P_1$, $P_2$, and $P_3$ due to the resistance values R1, R2, and R3 is essentially eliminated. Thus, a flow rate exiting any respective microneedle 178 is substantially the same, thereby facilitating a substantially equal distribution of the fluid across the entirety of the microneedle array 170.

In the exemplary embodiment, the pressures $P_7$, $P_8$, and $P_9$ at the downstream openings of the microneedles 178 are in the range between about 2 kPa (0.29 psi) to about 50 kPa (7.25 psi) and, in one suitable embodiment, are desired to be about 20 kPa (2.9 psi) to ensure sufficient pressure to distribute the fluid into a user's skin. In general, the pressure drop across a microneedle 178 is small such that the pressure on either side of a microneedle 178 is nearly the same. This enables the microneedle array assembly 80 to be substantially insensitive to resistance variability of the microneedles 178 because the resistance across the microneedles 178 is much smaller than the resistance across the distribution manifold 172. For example, in the exemplary embodiment, the pressure drop across the distribution manifold 172 is at least about 20 kPa (2.9 psi), which enables the pressure in the supply channels 192 to be substantially the same. Thus, a pressure in the supply channels 192 is in the range between about 32 kPa (4.6 psi) to about 80 kPa (11.6 psi), and, in one suitable embodiment, is desired to be at least about 50 kPa (7.25 psi) to ensure an outlet pressure of 20 kPa (2.9 psi) at the exit of the microneedle array 170.

In the exemplary embodiment, the bias member 156 is configured to maintain a generally continuous outlet pressure at or above about 20 kPa (2.9 psi) for at least about 90% of the fluid volume in the cavity 102 (shown in FIG. 2). For example, in one embodiment, the bias member 156 is configured to be a continuous or constant pressure device, for example a constant force coil spring that over a distance of travel of the plunger member 154 (shown in FIG. 2), the force is generally constant, or a change in the force is substantially small. In general, a typical coil spring will have a variable rate, i.e., the resistance of the spring to load varies during compression/extension. Thus, in the exemplary embodiment, if a typical variable rate bias member is used, as the bias member extends to force the fluid out of the upper cavity 102, the force exerted on the fluid would tend to decrease. This could result in an outlet pressure at the exit of the microneedle array 170 falling below the 20 kPa (2.9 psi) pressure desired to ensure the fluid is distributed the fluid into a user's skin. In another embodiment, the bias member 156 includes two parallel springs. For example, the bias member 156 may include a low force spring that has a first length, and a high force spring that has a second length that is shorter than the first length of the low force spring. Such a configuration enables the bias member 156 to have a pressure profile that is high pressure for a first period, and then a reduced pressure for a second period.

In addition to maintaining a generally constant outlet pressure, it is desired to have an increased initial pressure $P_{in}$ to facilitate a generally continuous fill rate of the fluid into the user's skin. If the bias member 156 is not a generally constant pressure device, or if the initial pressure exerted by the bias member is relatively low, the flow rate of the fluid into the user's skin can vary substantially with time. For example, a low initial pressure of a decaying amount of pressure can result in the initial increasing fill rate of the fluid into the user's skin slowing and/or stopping for a period of time. Many medicines benefit from having a steady state concentration in the patient's blood stream, thus it is desirable to maintain a generally continuous fill rate. It has be found that increasing the initial pressure of the bias member, while still maintaining the desired outlet pressure of 20 kPa (2.9 psi) at the exit of the microneedle array 170 facilitates maintaining a generally continuous and generally steady fill rate.

Figure 8:
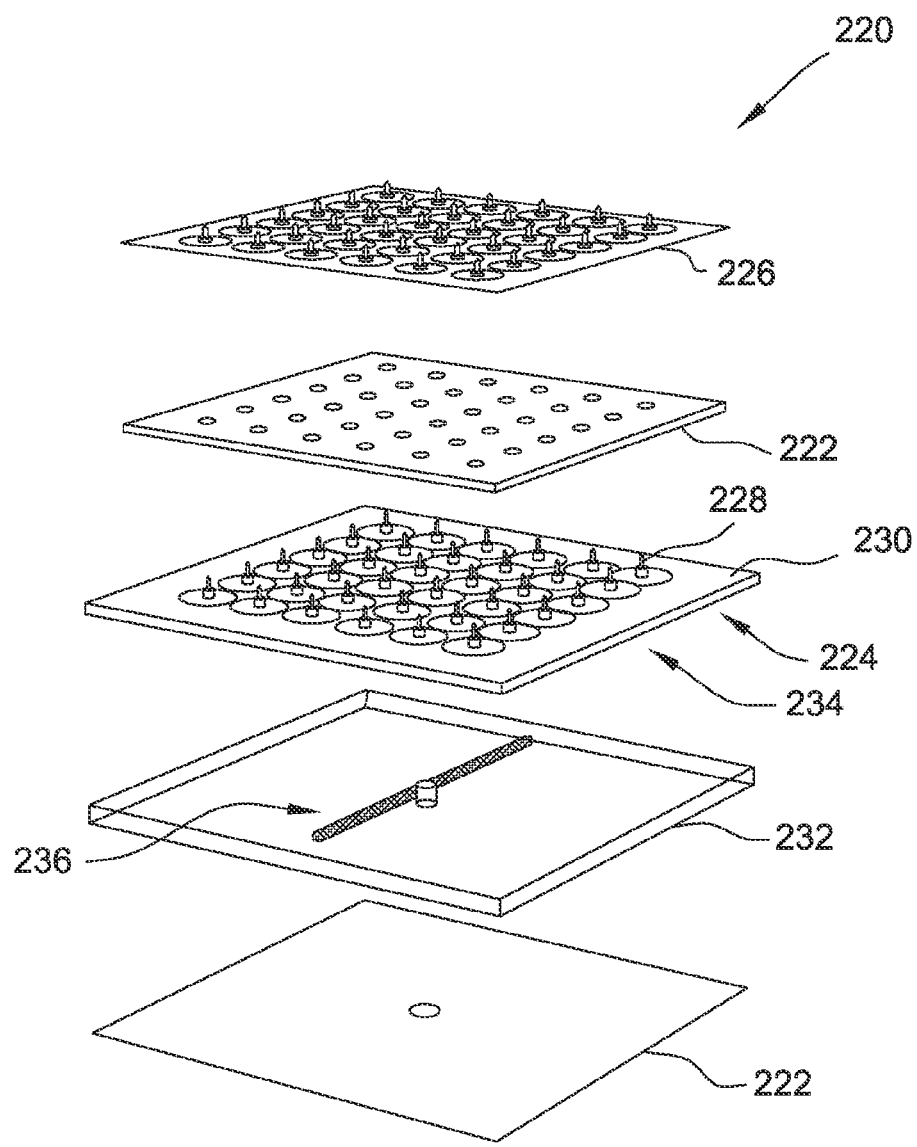
FIG. 8 is an exploded schematic of another exemplary microneedle array assembly for use with the fluid delivery apparatus shown in FIG. 1.
Figure 9:
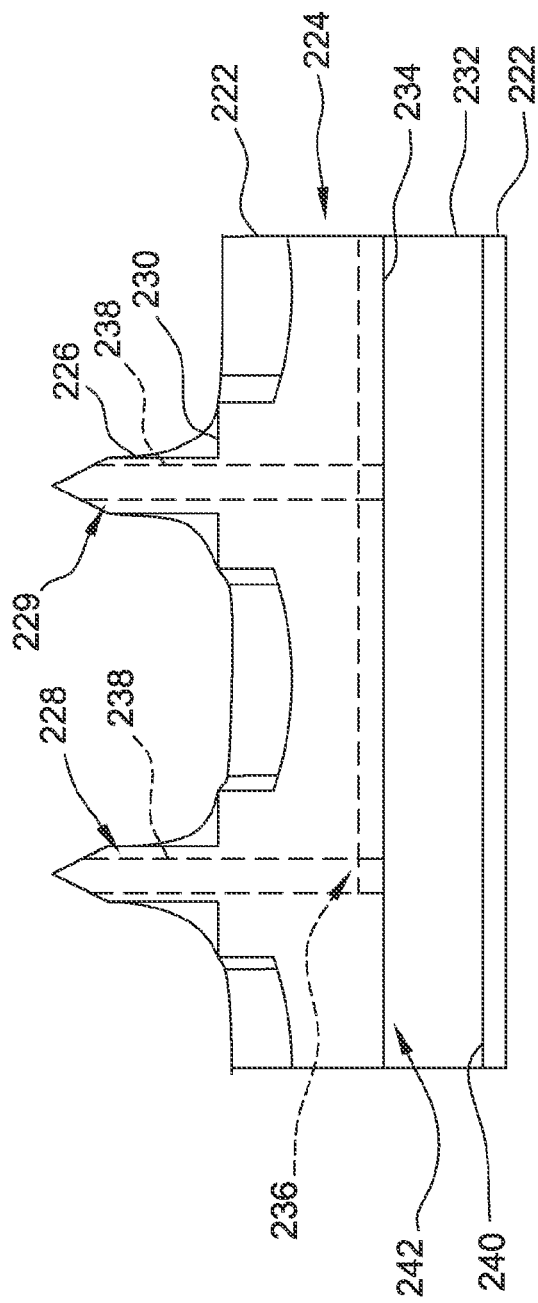
FIG. 9 is an enlarged, partial schematic cross-sectional view of the microneedle array assembly of FIG. 8.

FIG. 8 is an exploded schematic of another exemplary microneedle array assembly 220 for use with the fluid delivery apparatus 10 shown in FIG. 1. While the microneedle array assembly 220 is described herein as being used with the exemplary fluid delivery apparatus 10, it is contemplated that the microneedle array assembly 220 may be used, or otherwise incorporated into other suitable fluid delivery device. For example, the fluid delivery apparatus 10 may be replaced with other suitable devices for delivering a fluid to an inlet or inlet channel of the microneedle array 220. FIG. 9 is a schematic cross-sectional view of the microneedle array assembly 220 of FIG. 8. In the exemplary embodiment, the microneedle array assembly 220 is bonded to the mounting surface 74 via an adhesive layer 222. The microneedle array assembly 220 includes a microneedle array 224 and a membrane 226 draped at least partially across a plurality of microneedles 228 and a base surface 230 of the microneedle array 224. The microneedle array assembly 220 also includes a distribution manifold 232 that extends across a back surface 234 of the microneedle array 224 and is bonded thereto. The distribution manifold 232 includes a fluid distribution network 236 for providing a fluid to the microneedle array 224. The fluid supplied from the distribution manifold 232 may be in the form of a liquid drug formulation. The membrane-draped microneedles 228 are configured to penetrate a user's skin, such as for providing the liquid drug formulation into the user's skin by way of one or more apertures 238 formed in each microneedle 228.

In the exemplary embodiment, the draped membrane 226 is formed substantially identically to the draped membrane 174 described herein with respect to FIGS. 3 and 4. As with draped membrane 174, it is contemplated that microneedle array assembly 220 may be free of draped membrane 226 in some suitable embodiments.

In the exemplary embodiment, the microneedle array 224 may be fabricated from a rigid, semi-rigid, or flexible sheet of material, for example, without limitation, a metal material, a ceramic material, a polymer (e.g., plastic) material, or any other suitable material that enables the microneedle array 224 to function as described herein. For example, in one suitable embodiment, the microneedle array 224 may be formed from silicon by way of reactive-ion etching, or in any other suitable fabrication technique.

Figure 10:
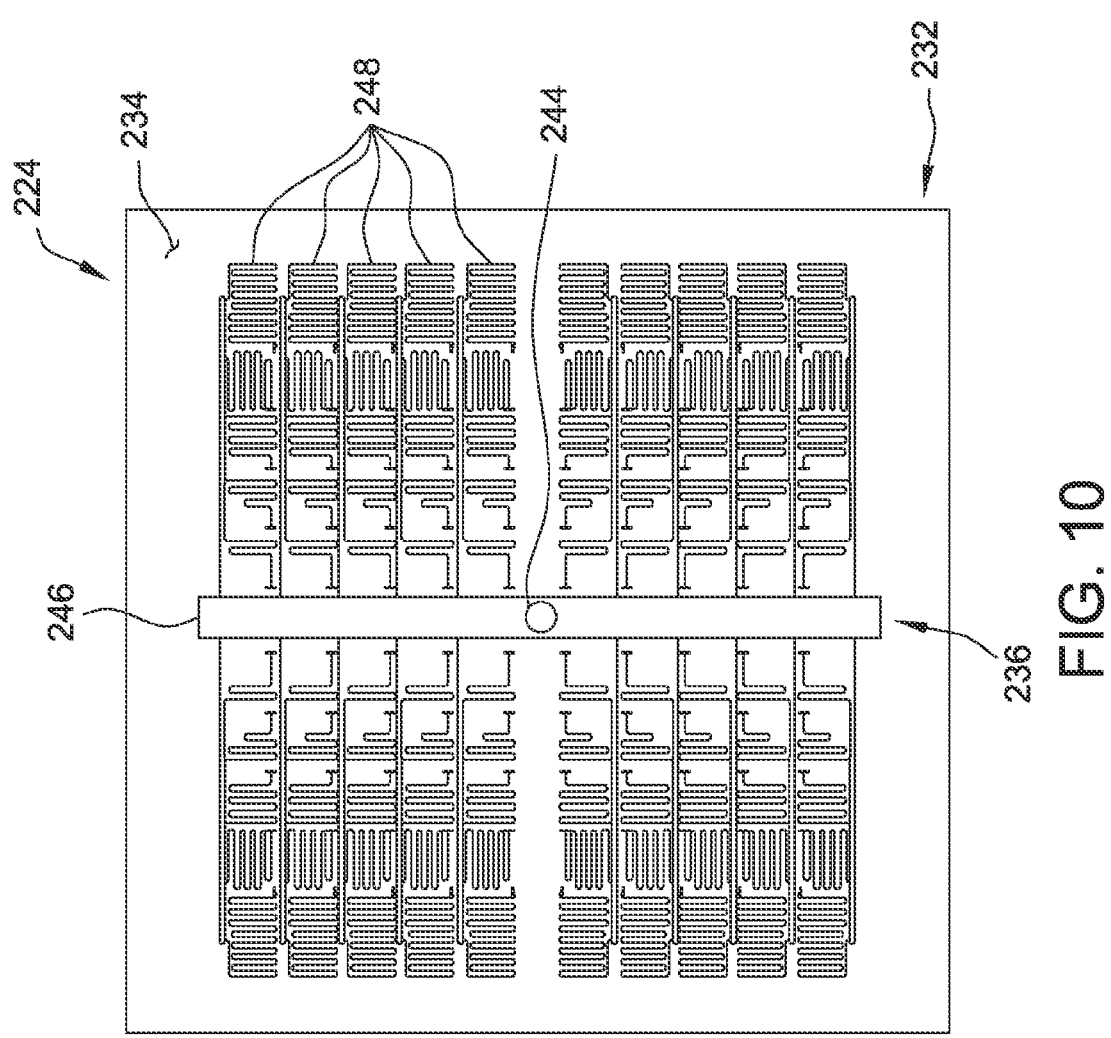
FIG. 10 is a schematic plan view of a back surface of the microneedle array for use with the microneedle array assembly of FIG. 8, including a distribution manifold.

FIG. 10 is a schematic plan view of the back surface 234 of the microneedle array 224 for use with the microneedle array assembly 220 of FIG. 8, including the distribution manifold 232. In the exemplary embodiment, the distribution manifold 232 includes the fluid distribution network 236 formed therein. The fluid distribution network includes, for example, a plurality of channels and/or apertures extending between a top surface 240 and a bottom surface 242 of the distribution manifold 232. The channels and/or apertures include a centrally-located inlet channel 244 coupled in flow communication with a supply channel 246 and the fluid passage 86 (shown in FIG. 1) of the microneedle array support structure 42 (Shown in FIG. 1). In the exemplary embodiment, the supply channel 246 extends longitudinally along the distribution manifold 232. The supply channel 246 facilitates distributing a fluid supplied by the inlet channel 244 across an area of the distribution manifold 232.

The supply channel 246 is coupled in flow communication to a plurality of supply troughs 248 formed in the back surface 234 of the microneedle array 224. The supply troughs 248 extend away from the supply channel 246 and are formed to create a resistance to a fluid flow that enables each of the supply troughs 248 to have a substantially identical fluid outlet pressure. For example, in one embodiment, the supply channels 246 form a tortuous flow path for the fluid, thereby facilitating an increase of the resistance of the supply troughs 248 to the flow of the fluid via a length of the channels. Each one of the supply troughs 248 are coupled in flow communication to the apertures 238 formed in each microneedle 228, as illustrated in FIG. 9. In other embodiments, the channels 246 and 248 may be formed in any configuration that enables the distribution manifold 232 to function as described herein. In the exemplary embodiment, the supply channel 246 and the supply troughs 248 have a generally rectangular shape substantially as described herein with respect to the supply channel 192 described in FIG. 6.

The inlet channel 244 may be formed in the distribution manifold 232 by drilling, cutting, etching, and or any other manufacturing technique for forming a channel or aperture through the distribution manifold. In the exemplary embodiment, the supply channel 246 is formed in the bottom surface 242 of the distribution manifold 232 using an etching technique. For example, in one suitable embodiment, wet etching, or hydrofluoric acid etching, is used to form the supply channel 246. For example, a mask is applied to the bottom surface 242 of the distribution manifold 232 to form the location of the channel to an accuracy of less than 2 micrometers, for example. As described herein, an etching material (e.g., hydrofluoric acid) is applied to the bottom surface 242 to remove material from the bottom surface, thereby forming the supply channel 246. In another suitable embodiment, DRIE or plasma etching may be used to create the supply channel 246. Alternatively, the supply channel 246 can be formed in bottom surface 242 using any fabrication process that enables the distribution manifold 232 to function as described herein. In the exemplary embodiment, the supply troughs are formed in the back surface 234 of the microneedle array 224 using the same etching techniques described with respect to the supply channel 246.

In the exemplary embodiment, the distribution manifold 232 and the microneedle array 224 are bonded together in face-to-face contact to seal the edges of and close the supply channel 246 and the supply troughs 248. In one suitable embodiment, direct bonding, or direct aligned bonding, is used by creating a prebond between the distribution manifold 232 and the microneedle array 224, as is described herein. In another suitable embodiment, anodic bonding is used to bond the distribution manifold 232 to the microneedle array 224. In an alternative embodiment, the distribution manifold 232 and the microneedle array 224 may be bonded together by using a laser-assisted bonding process, including applying localized heating to the distribution manifold 232 and the microneedle array 224 to bond them together.

In the exemplary embodiment, the distribution manifold 232 is fabricated from a glass material. Alternatively, the distribution manifold 232 may be fabricated from silicon. The microneedle array 224 is fabricated from silicon. However, in other embodiments, the microneedle array 224 may be fabricated from a glass material. It is contemplated that the distribution manifold 232 and the microneedle array 224 may be fabricated from any material and material combination that enables the microneedle array assembly 220 to function as described herein.

In this embodiment, the fluid enters the supply channel 246 via the inlet channel 244 and flows along and fills the supply channel 246 to distribute the fluid to the supply troughs 248 formed on the back surface 234 of the microneedle array 224. Each respective supply trough 248 for each individual microneedle 228 is different in length such that the flow rate from the inlet channel 244 of the distribution manifold 232 to the passageway 238 of the microneedle 228 is the same for all microneedles 228.

Figure 11:
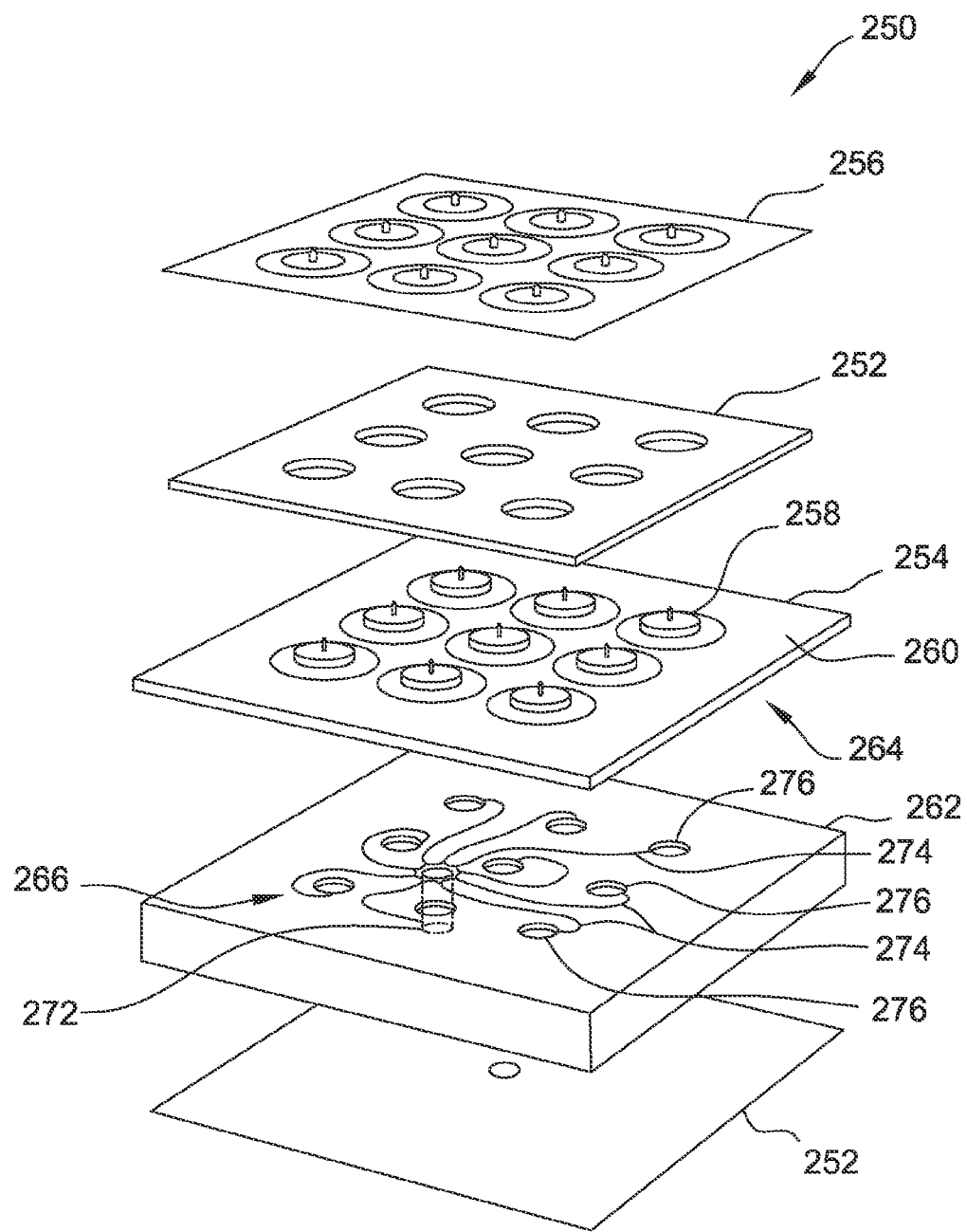
FIG. 11 is an exploded schematic of another exemplary microneedle array assembly for use with the fluid delivery apparatus shown in FIG. 1.
Figure 12:
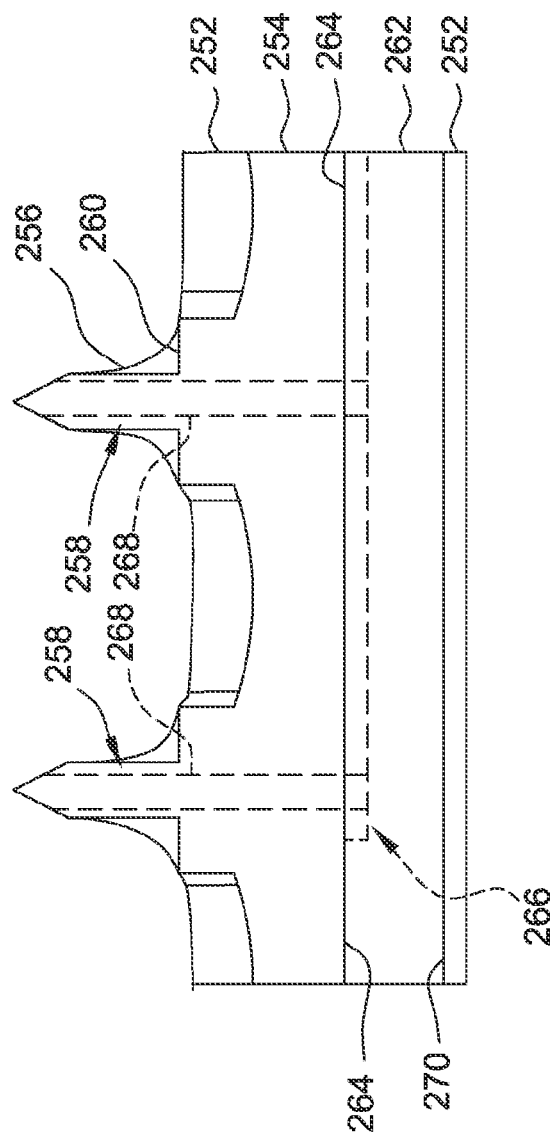
FIG. 12 is an enlarged, partial schematic cross-sectional view of the microneedle array assembly of FIG. 11.

FIG. 11 is an exploded schematic of another exemplary microneedle array assembly 250 for use with the fluid delivery apparatus 10 shown in FIG. 1. While the microneedle array assembly 250 is described herein as being used with the exemplary fluid delivery apparatus 10, it is contemplated that the microneedle array assembly 250 may be used, or otherwise incorporated into other suitable fluid delivery devices. For example, the fluid delivery apparatus 10 may be replaced with other suitable devices for delivering a fluid to an inlet or inlet channel of the microneedle array 250, FIG. 12 is a schematic cross-sectional view of the microneedle array assembly 250 of FIG. 11. In the exemplary embodiment, the microneedle array assembly 250 is bonded to the mounting surface 74 (shown in FIG. 1) via an adhesive layer 252. The microneedle array assembly 250 includes a microneedle array 254 of substantially the same construction of the microneedle array 170 described herein in relation to FIGS. 3 and 4, and a membrane 256 draped at least partially across a plurality of microneedles 258 and a base surface 260 of the microneedle array 254. The microneedle array assembly 250 also includes a distribution manifold 262 that extends across a back surface 264 of the microneedle array 254 and is bonded thereto. The distribution manifold 262 includes a fluid distribution network 266, including a plurality of channels 274 and/or apertures 272 and 276, for providing a fluid to the microneedle array 254. The membrane-draped microneedles 258 are configured to penetrate a user's skin, such as for providing the fluid into the user's skin by way of one or more apertures 268 formed in each microneedle 258.

In the exemplary embodiment, the draped membrane 256 is formed substantially identically to the draped membrane 174 described herein with respect to FIGS. 3 and 4. As with draped membrane 174, it is contemplated that microneedle array assembly 250 may be free of draped membrane 256 in some suitable embodiments.

In the exemplary embodiment, the microneedle array 254 may be fabricated from a rigid, semi-rigid, or flexible sheet of material, for example, without limitation, a metal material, a ceramic material, a polymer (e.g., plastic) material, or any other suitable material that enables the microneedle array 254 to function as described herein. For example, in one suitable embodiment, the microneedle array 254 is fabricated from silicon by way of reactive-ion etching, or in any other suitable fabrication technique.

Figure 13:
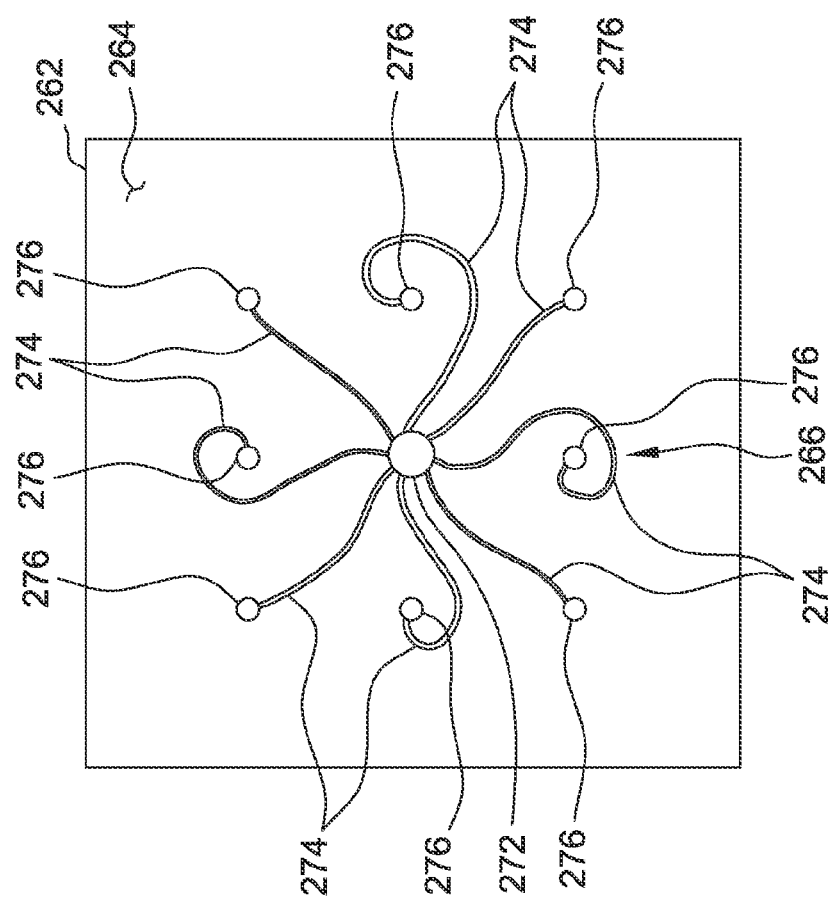
FIG. 13 is a schematic plan view of a back surface of a distribution manifold for use with the microneedle array assembly of FIG. 11.

FIG. 13 is a schematic plan view of a back surface 264 of the distribution manifold 262 for use with the microneedle array assembly 250 of FIG. 11. In the exemplary embodiment, the distribution manifold 262 includes the fluid distribution network 266 formed therein. The fluid distribution network includes, for example, a plurality of channels and/or apertures extending between a top surface 270 and the back surface 264 of the distribution manifold 262. The channels and/or apertures include a centrally-located inlet channel 272 coupled in flow communication with a plurality of supply channels 274 and the fluid passage 86 (shown in FIG. 1) of the microneedle array support structure 42 (shown in FIG. 1). In the exemplary embodiment, the supply channels 274 extend along the distribution manifold 262, forming a tortuous path for the fluid, thereby facilitating an increase of the resistance of the supply channels 274. The supply channels 274 facilitate distributing a fluid supplied by the inlet channel 272 across an area of the distribution manifold 262.

Each of the supply channels 274 is coupled in flow communication to an outlet channel 276. Each outlet channel 276 is generally aligned with a respective microneedle 258 for distributing the fluid through the passageways 268 of the microneedles 258, as illustrated in FIG. 12. In other embodiments, the supply channels 274 and the outlet channels 276 may be formed in any configuration that enables the distribution manifold 262 to function as described herein. In the exemplary embodiment, the supply channels 274 have a generally rectangular shape substantially as described herein with respect to the supply channel 192 described in FIG. 6.

The inlet channel 272 may be formed in the distribution manifold 262 by drilling, cutting, etching, and or any other manufacturing technique for forming a channel or aperture through the distribution manifold. In the exemplary embodiment, the supply channels 274 are formed on the bottom surface 268 of the distribution manifold 262 by molding the set of channels 274 into the distribution manifold 262. Alternatively, the supply channels 274 can be formed on bottom surface 268 using any fabrication process that enables the distribution manifold 262 to function as described herein.

In the exemplary embodiment, the distribution manifold 262 and the microneedle array 254 are bonded together in face-to-face contact to seal the edges of and close the supply channels 274. In one suitable embodiment, direct bonding, or direct aligned bonding, is used by creating a prebond between the distribution manifold 262 and the microneedle array 254, as is described herein. In another suitable embodiment, anodic bonding is used to bond the distribution manifold 262 to the microneedle array 254. In an alternative embodiment, the distribution manifold 262 and the microneedle array 254 may be bonded together by using a laser-assisted bonding process, including applying localized heating to the distribution manifold 262 and the microneedle array 254 to bond them together.

In the exemplary embodiment, the distribution manifold 262 is fabricated from a polydimethylsiloxane (PDMS) polymer. Alternatively, the distribution manifold 232 may be fabricated from any material and material combination that enables the microneedle array assembly 250 to function as described herein.

In this embodiment, the fluid enters the supply channels 274 via the inlet channel 272 and flows along and fills the supply channels 274 to distribute the fluid to each individual microneedle 258. Each supply channel 274 is substantially the same length such that the total flow resistance from the inlet channel 272 of the distribution manifold 262 to the passageway 268 of the microneedle 258 is the same for all microneedles 258. Thus, because a resistance to each microneedle 258 is substantially the same, the flow rate is also substantially the same to all microneedles 258. The path of the individual supply channels 274 is determined based on the location of the respective microneedle 258 that the channel is connected to.

The apparatus, system, and methods described in detail herein enable a microneedle array assembly to distribute a substantially equal quantity of a medicine through each microneedle of the microneedle assembly. A microfluidic distribution manifold for use with a microneedle assembly includes fluid supply channel features that enable a total flow resistance in each supply channel to be substantially equal, thereby generating an equalized flow rate. In addition, the resistance levels of the flow channels can be configured to enable a substantially constant flow rate of the fluid over an extended period of time, thereby facilitating a steady state concentration of the fluid in the user's blood stream.

Exemplary embodiments of an apparatus, system, and methods for a microfluidic distribution manifold are described above in detail. The apparatus, system, and methods described herein are not limited to the specific embodiments described, but rather, components of apparatus, systems, and/or steps of the methods may be utilized independently and separately from other components and/or steps described herein. For example, the methods may also be used in combination with other fluid delivery apparatus, systems, and methods, and are not limited to practice with only the apparatuses, systems, and methods described herein. Rather, the exemplary embodiments can be implemented and utilized in connection with many fluid delivery applications.

Although specific features of various embodiments of the disclosure may be shown in some drawings and not in others, this is for convenience only. In accordance with the principles of the disclosure, any feature of a drawing may be referenced and/or claimed in combination with any feature of any other drawing.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

As various changes could be made in the above embodiments without departing from the scope of the disclosure, it is intended that all matter contained in the above description and shown in the accompanying drawings shall be interpreted as illustrative and not in a limiting sense.

What is claimed is:

1. A microneedle array assembly, comprising:
a microneedle array comprising a plurality of microneedles; and
a distribution manifold comprising a supply channel coupled in flow communication to a plurality of resistance channels,
each resistance channel coupled in flow communication to a respective one of a plurality of outlet channels, and
each outlet channel coupled in flow communication to a respective one of the plurality of microneedles,
wherein a resistance value to a fluid flow through each resistance channel of the plurality of resistance channels is in a range between about 5 times greater to about 100 times greater than a resistance to the fluid flow through the supply channel.

2. The microneedle array assembly in accordance with claim 1, wherein the resistance value to the fluid flow through each resistance channel of the plurality of resistance channels is at least about 30 times greater than a resistance to the fluid flow through the supply channel.

3. The microneedle array assembly in accordance with claim 1, wherein each resistance channel of the plurality of resistance channels forms a tortuous flow path for the fluid flow for increasing the resistance of the resistance channel to the fluid flow.

4. The microneedle array assembly in accordance with claim 1, wherein the distribution manifold comprises a base substrate coupled to a cover substrate to define the supply channel and the plurality of resistance channels.

5. The microneedle array assembly in accordance with claim 1, wherein the distribution manifold further comprises an inlet channel coupled upstream in flow communication to the supply channel and the plurality of outlet channels, each outlet channel of the plurality of outlet channels coupled downstream in flow communication to a respective one of the resistance channels.

6. The microneedle array assembly in accordance with claim 5, wherein a pressure drop between the inlet channel and each outlet channel of the plurality of outlet channels is substantially the same.

7. The microneedle array assembly in accordance with claim 1, wherein the distribution manifold is fabricated from one or more of a glass, a silicon, and a polydimethylsiloxane (PDMS) polymer.

8. The microneedle array assembly in accordance with claim 1, wherein a pressure of the fluid flow at an exit of each microneedle of the plurality of microneedles is in a range between about 2 kPa to about 50 kPa.

9. A fluid delivery apparatus comprising:
a reservoir containing a fluid; and
a microneedle array assembly comprising:
a microneedle array comprising a plurality of fluid channels formed in an upstream side and a plurality of microneedles extending from a downstream side, each microneedle coupled in flow communication to a respective one of a plurality of outlet channels,
and each outlet channel coupled in flow communication to a respective one of the plurality of fluid channels; and
a distribution manifold comprising a supply channel coupled in flow communication to the plurality of fluid channels,
wherein a resistance value to a fluid flow through each fluid channel of the plurality of fluid channels is in a range between about 5 times greater to about 100 times greater than a resistance to the fluid flow through the supply channel.

10. The fluid delivery apparatus in accordance with claim 9, wherein the resistance value to the fluid flow through each fluid channel of the plurality of fluid channels is at least about 30 times greater than a resistance to the fluid flow through the supply channel.

11. The fluid delivery apparatus in accordance with claim 9, wherein each fluid channel of the plurality of fluid channels forms a tortuous flow path for the fluid flow for increasing the resistance of the fluid channel to the fluid flow.

12. The fluid delivery apparatus in accordance with claim 9 further comprising a bias member for causing at least some of the fluid to flow from the reservoir toward the microneedle array assembly.

13. The fluid delivery apparatus in accordance with claim 12, wherein the bias member is configured to maintain a pressure of the fluid flow at an exit of each microneedle of the plurality of microneedles at or above about 20 kPa (2.9 psi) until at least about 90% of a fluid volume of the fluid has flowed from the reservoir.

14. The fluid delivery apparatus in accordance with claim 9, wherein the distribution manifold further comprises an inlet channel coupled upstream in flow communication to the supply channel and the reservoir.

15. The fluid delivery apparatus in accordance with claim 14, wherein a pressure drop between the inlet channel and each microneedle of the plurality of microneedles substantially the same.

16. The fluid delivery apparatus in accordance with claim 9, wherein the distribution manifold is fabricated from one or more of a glass, a silicon, and a polydimethylsiloxane (PDMS) polymer.

17. The fluid delivery apparatus in accordance with claim 9, wherein a pressure of the fluid flow at an exit of each microneedle of the plurality of microneedles is in the range between about 2 kPa to about 50 kPa.

18. A microneedle array assembly, comprising:
a microneedle array comprising a plurality of microneedles, each microneedle of the plurality of microneedles comprising an aperture; and
a distribution manifold comprising an inlet channel, a plurality of supply channels formed in a downstream surface of the distribution manifold, and a plurality of outlet channels, each supply channel coupled in flow communication to the inlet channel and a respective one of the plurality of outlet channels, and each outlet channel coupled in flow communication to a respective one of the plurality of microneedles, wherein a pressure drop between the inlet channel and each outlet channel of the plurality of outlet channels is substantially the same.

19. The microneedle array assembly in accordance with claim 18, wherein each supply channel of the plurality of supply channels forms a tortuous flow path for a fluid flow for increasing a resistance of the supply channel to the fluid flow.

20. The microneedle array assembly in accordance with claim 18, wherein the distribution manifold is fabricated from one or more of a glass, a silicon, and a polydimethylsiloxane (PDMS) polymer.

\* \* \* \* \*